United States Patent [19]

Grozinger et al.

[11] Patent Number: 4,788,198
[45] Date of Patent: Nov. 29, 1988

[54] DIAZINE-ETHYENYLPHENYL OXAMIC ACIDS AND ESTERS AND SALTS THEREOF

[75] Inventors: Karl G. Grozinger, Ridgefield; James T. Oliver, Middlebury, both of Conn.

[73] Assignee: Boehringer Ingelheim Pharmaceuticals, Inc., Ridgefield, Conn.

[21] Appl. No.: 43,018

[22] Filed: Apr. 27, 1987

Related U.S. Application Data

[60] Division of Ser. No. 733,007, May 10, 1985, Pat. No. 4,681,884, which is a continuation-in-part of Ser. No. 528,522, Sep. 1, 1983, abandoned.

[51] Int. Cl.$^4$ ............... C07D 241/06; C07D 241/08; A61K 31/495
[52] U.S. Cl. .................................. 514/255; 544/336; 544/408; 544/409; 544/410; 514/247
[58] Field of Search ............... 514/255; 544/336, 408, 544/409, 410

[56] References Cited

U.S. PATENT DOCUMENTS

| | | | |
|---|---|---|---|
| 3,953,468 | 4/1976 | Wechter et al. | 544/362 |
| 3,966,965 | 6/1976 | Sellstedt et al. | 544/336 |
| 4,054,666 | 10/1977 | Sellstedt et al. | 514/371 |
| 4,061,791 | 12/1977 | Hall et al. | 514/533 |
| 4,238,496 | 12/1980 | Hess et al. | 514/234 |

FOREIGN PATENT DOCUMENTS

| | | | |
|---|---|---|---|
| 97942 | 1/1984 | European Pat. Off. | 544/336 |
| 2362409 | 6/1974 | Fed. Rep. of Germany . | |
| 2525226 | 12/1975 | Fed. Rep. of Germany . | |
| 24562 | 2/1983 | Japan | 544/336 |

OTHER PUBLICATIONS

Vladimintsev et al., Chem. Abs, 90:49472c (1979).

Primary Examiner—Donald G. Daus
Assistant Examiner—F. Bernhardt
Attorney, Agent, or Firm—David E. Frankhouser; Alan R. Stempel; Mary Ellen M. Timbers

[57] ABSTRACT

Compounds of the formula

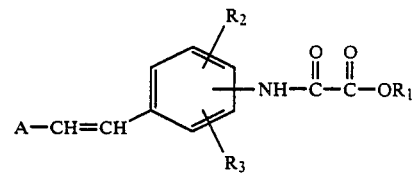

$R_1$ is hydrogen or alkyl of 1 to 4 carbon atoms;
$R_2$ is hydrogen, methyl, hydroxyl, alkoxy of 1 to 4 carbon atoms, di(alkyl of 1 to 2 carbon atoms)amino-(alkoxy of 1 to 4 carbon atoms) or NHCOCOOR$_1$;
$R_3$ is hydrogen or NHCOCOOR$_1$;
A is $R_4$ is hydrogen, methyl, alkoxy of 1 to 4 carbon atoms, hydroxyl, amino, alkanoyloxy of 1 to 2 carbon atoms, di(alkyl of 1 to 2 carbon atoms)-amino-(alkoxy of 1 to 4 carbon atoms) or acetamido; and
$R_5$ is hydrogen, amino, alkoxy of 1 to 4 carbon atoms, halogen or NHCOCOOR$_1$;

and, when $R_1$ is hydrogen, nontoxic, pharmaceutically acceptable salts thereof. The compounds as well as their salts are useful for the treatment of immunological, inflammatory and allergic disorders such as asthma, rhinitis, conjunctivitis, hay fever, urticaria, food allergies and the like.

15 Claims, No Drawings

DIAZINE-ETHYENYLPHENYL OXAMIC ACIDS AND ESTERS AND SALTS THEREOF

This is a division of U.S. Ser. No. 733,007, filed on May 10, 1985, now U.S. Pat. No. 4,681,884, which is a continuation-in-part of U.S. Ser. No. 528,522, filed on Sept. 1, 1983, now abandoned.

This invention relates to novel diazine-ethenylphenyl oxamic acids and esters and salts thereof, to methods of preparing these compounds, to pharmaceutical compositions containing them as active ingredients, and to methods of using them for the treatment of immunological, inflammatory and allergic disorders.

THE PRIOR ART

Cromoglycate, normally administered as the sodium salt, is a potent and useful antiallergic, commonly prescribed for the treatment of bronchial asthma. Cromoglycate has for many years been accepted as an effective bronchodilator when given by inhalation as a solid. However, it is known to have certain disadvantages; for instance, it is not active when given orally, which warrants a search for new orally active antiallergics.

A number of oxamate derivatives have been disclosed in the patent and scientific literature. Illustrative of such prior art are the following:
  (a) 4-Substituted thiazol-2-oxamic acids, U.S. Pat. No. 4,238,496 and
  (b) N,N'-(Phenylene)dioxamic acid and its derivatives, German Offenlegungsschrift No. 2,362,409.

The prior art, however, does not disclose diazine-ethenylphenyl oxamic acids or their esters or salts.

SUMMARY OF THE INVENTION

The present invention relates to novel diazine-ethenylphenyl oxamic acids and esters of formula I

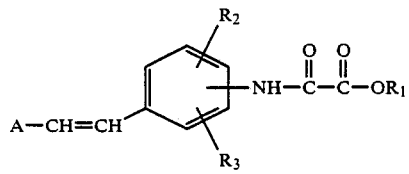

wherein
$R_1$ is hydrogen or alkyl of 1 to 4 carbon atoms;
$R_2$ is hydrogen, methyl, hydroxyl, alkoxy of 1 to 4 carbon atoms, di(alkyl of 1 to 2 carbon atoms)amino(alkoxy of 1 to 4 carbon atoms) or halogen;
$R_3$ is hydrogen or $NHCOCOOR_1$;
A is

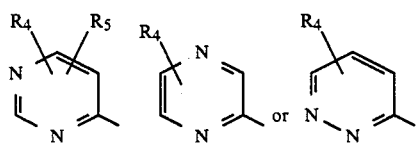

$R_4$ is hydrogen, halogen, methyl, alkoxy of 1 to 4 carbon atoms, hydroxyl, amino, alkanoyloxy of 1 to 2 carbon atoms, di(alkyl of 1 to 2 carbon atoms)-amino-(alkoxy of 1 to 4 carbon atoms or acetamido; and
$R_5$ is hydrogen, amino, alkoxy of 1 to 4 carbon atoms, or $NHCOCOOR_1$;

and, when $R_1$ is hydrogen, nontoxic, pharmaceutically acceptable salts thereof, especially their alkali metal and primary or secondary amine salts.

In subgeneric aspects, the invention comprehends compounds of formula I wherein
$R_1$ is hydrogen or ethyl,
$R_2$ is hydrogen,
$R_3$ is $—NHCOCOOR_1$
A is

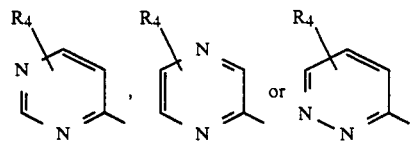

$R_4$ is hydrogen or methyl, and nontoxic, pharmaceutically acceptable salts thereof.

The compounds of the present invention, that is, those embraced by formula I above and their nontoxic, pharmaceutically acceptable salts, exhibit immunological, anti-inflammatory and anti-allergic activities in warm-blooded animals such as rats. They are useful for the treatment of mammals suffering allergic or inflammatory disorders such as asthma, rhinitis, conjunctivitis, hay fever, urticaria, food allergies and the like.

DETAILED DESCRIPTION OF THE PREFERRED EMBODIMENTS

Although specific terms are used in the following description for clarity, they refer only to the particular embodiment(s) selected for illustration, and are not intended to limit the scope of the invention.

The compounds of the present invention can be prepared by several methods, selected ones of which are described below. The starting materials used in the examples are commercially available or can be synthesized by well known published procedures from commercially available materials unless otherwise fully described here. Standard reagent grade chemicals are used in these preparations and in the working examples which follow unless otherwise specifically indicated.

The compounds embraced by Formula I can be prepared from a [2-(aminophenyl)ethyl]diazine (II)

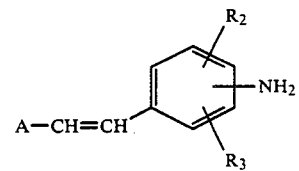

wherein A, $R_2$ and $R_3$ have the same meanings as in Formula I by treating it with an oxalate halide, preferably the chloride, or with a dialkyl oxalate, optionally followed by hydrolysis of the ester group.

The reaction is carried out by dissolving or suspending the [2-(aminophenyl)ethenyl]diazine starting material (II) or an acid addition salt thereof, in an inert liquid medium, and admixing the oxalic acid derivative, e.g. the oxalate halide or dialkyl oxalate, dropwise with the solution or suspension. Examples of suitable inert liquid media are benzene, toluene, xylene, methylene chloride, dimethylformamide or tetrahydrofuran. In addition, it is preferred to add an organic base, such as pyridine or triethylamine, to the reaction mixture to neutralize the acid released by the reaction. Since the reaction is strongly exothermic, the oxalic acid derivative should be added slowly and, if necessary, while cooling.

Since most [2-(aminophenyl)ethenyl]diazines (II) are sparsely soluble, it is of advantage to let the reaction mixture stand for an extended period of time, for instance overnight, with or without stirring, before isolating the reaction product.

The reaction mixture is then processed in conventional manner, that is, by evaporating the inert liquid medium, extracting the residue with a suitable solvent or solvent mixture, such as ether, ethyl acetate, chloroform, hexane or mixtures of any two or more of these, purifying the extract solution, evaporating the solvent, and recrystallizing the residue. In some cases further purification by column chromatography is of advantage.

If it is desired to obtain an end product of the Formula I wherein $R_1$ is hydrogen, the ester group is removed by hydrolysis with a basic or acid catalyst. Suitable such catalysts are strong bases such as sodium hydroxide or potassium hydroxide, or mineral acids such as hydrochloric acid, sulfuric acid or phosphoric acid.

The [2-(aminophenyl)ethenyl]diazines (II) are prepared by a process which comprises (a) Reaction of a nitrobenzaldehyde (III) with a methyldiazine [pyrimidine (IVA), pyrazine (IVB) or pyridazine (IVC)]in a suitable solvent such as acetic anhydride, formic acid or the like to produce a corresponding [2-(nitrophenyl)ethenyl]diazine (VA, VB or VC) pursuant to the following reaction scheme:

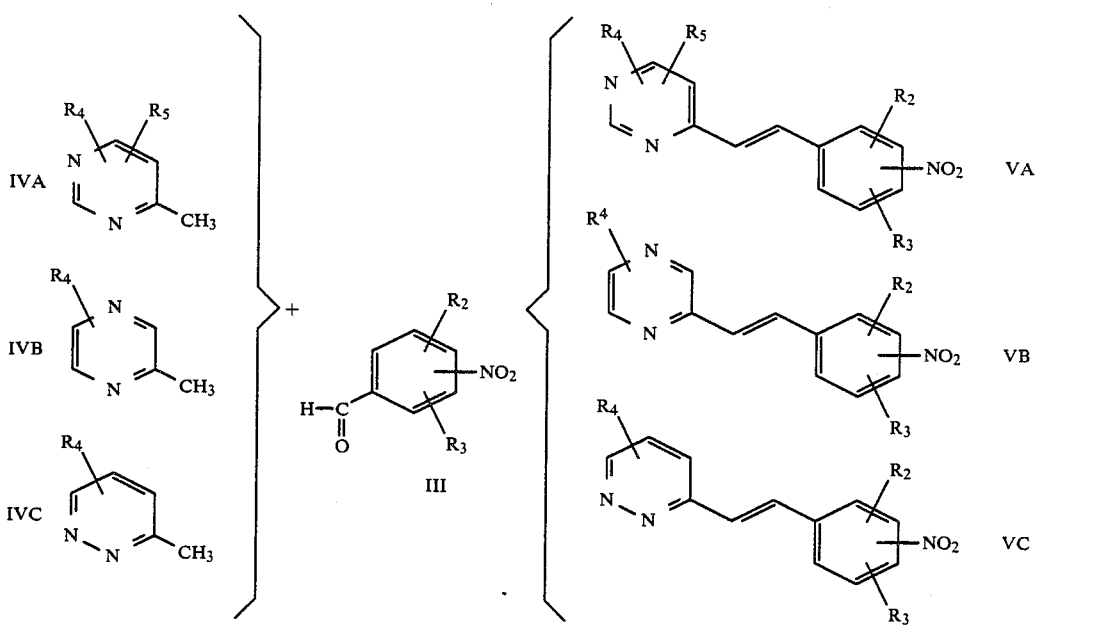

(b) and, thereafter, reduction of the [2-(nitrophenyl)ethenyl]diazine (VA, VB or VC) to the corresponding amine (i) with a metal or metal salt, such as iron, tin or zinc, in an aqueous acid according to A. J. Bechamp, Ann. Chim. Phys. [3] 42, 186, (1854), or (ii) catalytically with hydrogen using Raney Nickel as a catalyst in a suitable solvent such as ethanol or tetrahydrofuran; or with hydrazine in the presence of a catalyst, such as palladium.

The preparation of some [2-(nitrophenyl)ethenyl]diazine derivatives is described in the literature. For example, 4-[2-(p-nitrophenyl)ethenyl]2-aminopyrimidine

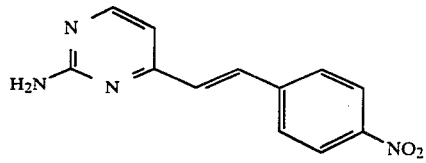

can be prepared according to the procedure disclosed in Chemical Abstracts 62: 19448c (Japanese Pat. No. 19652, 1964). Similarly, the compounds

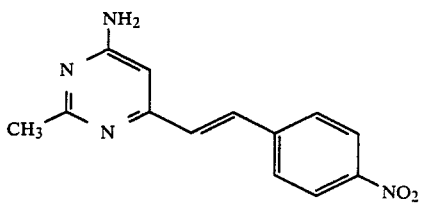

and

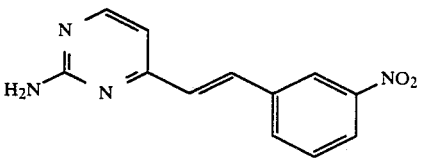

can be prepared by the general procedures described in J. Med. Chem. 1290 (1970), J. Chem. Soc. C 1343 (1967) and J. Pharm. Soc. Jap. 72, 909 (1953).

The following examples illustrate the present invention and enable others skilled in the art to understand it more completely. However, the invention is not limited solely to the particular examples given below.

EXAMPLE 1

Ethyl 2-(4-pyrimidinyl)ethenylphenyl-4 oxamate

Ethyl oxalyl chloride (1.2 g) is added dropwise to a suspension of 4-[2-(p-aminophenyl)ethenyl]-pyrimidine (1.3 g) in methylene chloride (30 ml) containing pyridine (1.6 ml), and the mixture is stirred overnight at room temperature. Thereafter, the reaction mixture is washed first with an aqueous sodium bicarbonate solution, then with water and then with a saturated aqueous sodium chloride solution, dried over magnesium sulfate and finally evaporated to dryness. The residue is recrystallized from chloroform and petroleum ether, and gives ethyl 2-(4-pyrimidinyl)ethenylphenyl-4 oxamate (1.3 g), which has a melting point of 171°–173° C.

The starting compound is prepared as follows. p-Nitrobenzaldehyde (24.2 g), 4-methyl-pyrimidine (15.5 g) and acetic anhydride (16.7 g) are mixed at room temperature, and the mixture is heated at 120° C. for 5 hours. After cooling, the mixture is poured into water (500 ml), and the aqueous mixture is extracted several times with chloroform. The combined chloroform extracts are dried over magnesium sulfate and concentrated until crystals separated. Addition of ether gives 4-[2-(p-nitrophenyl)ethenyl]pyrimidine (28 g), m.p. 213°–215° C.

Hydrochloric acid (100 ml of 4N) is added dropwise to a mixture of 4-[2-(p-nitrophenyl)ethenyl]pyrimidine (28 g), ethanol (250 ml) and iron filings (28 g). The reaction temperature is increased to 65° C., and the mixture is stirred at that temperature for two hours. Water is added, followed by an aqueous 30% potassium hydroxide solution (200 ml), and chloroform (1 liter). The mixture is filtered through celite, and the chloroform layer is separated, dried over sodium sulfate and then concentrated. Addition of ether gives 4-[2-(p-aminophenyl)ethenyl]pyrimidine (10.3 g), m.p. 227°–230° C., which is used as the starting compound without further purification.

EXAMPLE 2

2-(4-Pyrimidinyl)ethenylphenyl-4 oxamic acid and its ethanolamine salt

Sodium hydroxide solution (13.5 ml of a 1N) is added dropwise to a suspension of ethyl 4-[2-(4-pyrimidinyl)ethenyl]phenyl oxamate (4 g) (see Example 1) in water (50 ml) and ethanol (50 ml) while vigorously stirring until a clear solution is formed. The resulting solution is acidified with 2N hydrochloric acid, and the precipitate formed thereby is filtered off. The filter cake is dried to give 2-(4-pyrimidinyl)ethenylphenyl-4 oxamic acid (2 g), m.p. 214°–216° C.

The acid is suspended in a mixture of N,N-dimethyl formamide (50 ml), and ethanolamine (1 g), and the precipitate formed thereby is filtered off and washed with ether. The ethanolamine salt (1.3 g) of the acid compound, m.p. 202°–205° C., is obtained.

EXAMPLE 3

Ethyl 2-(2-ethoxyoxalylaminopyrimidin-4-yl)-ethenylphenyl-4 oxamate

Ethyl oxalyl chloride (19 ml) is added dropwise to a solution of 4-[2-(p-aminophenyl)ethenyl]-2-aminopyrimidine (13.5 g) in dry pyridine (75 ml). The reaction mixture is then stirred (12 hours) at room temperature. The progress of the reaction is periodically checked by thin-layer chromatography. After the completion of the reaction, the reaction mixture is poured into ice water. The crude product is extracted with chloroform, dried and purified on a silica gel column. After recrystallization from chloroform and ether, ethyl 2-[2-(ethoxyoxalylaminopyrimidin-4-yl)ethenyl]phenyl-4 oxamate (9.0 g), m.p. 191°–193° C., is obtained.

The starting compound is prepared as follows. A solution of 2-amino-4-methylpyrimidine (21.8 g) and p-nitrobenzaldehyde (30.2 g) in formic acid (45 ml) is refluxed (24 hours). After cooling, the reaction mixture is poured into water (1 liter), and the aqueous mixture is neutralized with a 5N sodium hydroxide solution. The crude product is extracted with chloroform, and the extract is dried over sodium sulfate and concentrated to dryness. The crude product is purified on a silica gel column to give 4-[2-(p-nitrophenyl)ethyenyl]-2-aminopyrimidine (27.8 g), m.p. 214°–216° C., which is used for the next step without purification.

Hydrochloric acid (100 ml of 4N) is added dropwise to a stirred mixture of 4-[2-(p-nitrophenyl)-ethenyl]-2-aminopyrimidine (21.8 g), ethanol (250 ml) and iron filing (22 g). During the addition the reaction temperature is increased to 65° C., and stirring is continued (2 hours) at 65° C. Water is added, followed by an aqueous 30% sodium hydroxide solution (200 ml) and chloroform (1 liter). The chloroform layer is then separated and dried over sodium sulfate. After evaporation and addition of ether, 4-[2-(p-aminophenyl)-ethenyl]-2-aminopyrimidine is obtained (13.5 g), which is used as the starting compound without further purification.

Using the appropriate starting compounds and the procedures described in the preceding examples the following compounds of the formula

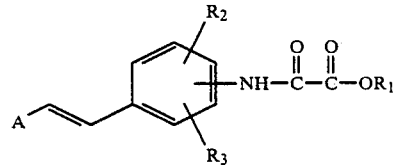

where also prepared:

| Example No. | Nomenclature | A | $R_2$ | $R_3$ | NHCOCOOR$_1$ | m.p. °C. |
|---|---|---|---|---|---|---|
| 4 | Ethyl 2-(4-pyrimidinyl)ethenyl phenyl-3 oxamate | 4-pyrimidinyl | H | H | 3-NHCOCOOC$_2$H$_5$ | 127–128 |
| 5 | 2-(4-Pyrimidinyl)ethenylphenyl-3 oxamic acid ethanolamine salt | 4-pyrimidinyl | H | H | 3-NHCOCOOH Ethanolamine salt | 161–163 |
| 6 | Ethyl 2-(4-pyrimidinyl)ethenyl phenyl-2 oxamate | 4-pyrimidinyl | H | H | 2-NHCOCOOC$_2$H$_5$ | 105–110 |
| 7 | 2-(4-Pyrimidinyl)ethenylphenyl-2 oxamic acid ethanolamine salt | 4-pyrimidinyl | H | H | 2-NHCOCOOH Ethanolamine salt | 151–153 |
| 8 | Ethyl 2-(4-pyrimidinyl)ethenyl-2-hydroxphenyl-4 oxamate | 4-pyrimidinyl | 2-OH | H | 4-NHCOCOOC$_2$H$_5$ | 145–147 |
| 9 | Ethyl 2-(4-pyrimidinyl)ethenyl-6-chlorophenyl-3 oxamate | 4-pyrimidinyl | 6-Cl | H | 3-NHCOCOOC$_2$H$_5$ | 147–148 |
| 10 | Ethyl 2-(4-pyrimidinyl)ethenyl-3-N,N—dimethylamino-ethoxphenyl-4 oxamate | 4-pyrimidinyl | 3-OCH$_2$CH$_2$—N(CH$_3$)$_2$ | H | 4-NHCOCOOC$_2$H$_5$ | 156–159 |
| 11 | Ethyl 2-(4-pyrimidinyl)ethenyl-4- oxamate | 4-pyrimidinyl | 4-OCH$_2$CH$_2$—N(CH$_3$)$_2$ | H | 3-NHCOCOOC$_2$H$_5$ sesquihydro-chloride | 176–178 |

| Example No. | Nomenclature | A | R₂ | R₃ | NHCOCOOR₁ | m.p. °C. |
|---|---|---|---|---|---|---|
| 12 | Diethyl 2-(4-pyrimidinyl)ethenyl phenyl-2,4 dioxamate | 4-pyrimidinyl | 2-NHCOCO—OC₂H₅ | H | 4-NHCOCOOC₂H₅ | 135–137 |
| 13 | Ethyl 2-(2,6-diethoxypyrimidin-4-yl)ethenylphenyl-4 oxamate | 2,6-diethoxypyrimidin-4-yl | H | H | 4-NHCOCOOC₂H₅ | 156–159 |
| 14 | Ethyl 2-(2-methyl-6-aminopyrimidin-4-yl)ethenyl phenyl-4 oxamate | 2-methyl-6-aminopyrimidin-4-yl | H | H | 4-NHCOCOOC₂H₅ | 267–269 |
| 15 | Ethyl 2-(6-methylpyrimidin-4-yl) ethenylphenyl-4 oxamate | 6-methylpyrimidin-4-yl | H | H | 4-NHCOCOOC₂H₅ | 149–151 |
| 16 | Ethyl 2-(2-acetamidopyrimidin-4-yl)ethenylphenyl-3 oxamate | 2-acetamidopyrimidin-4-yl | H | H | 3-NHCOCOOC₂H₅ | 234–236 |
| 17 | 2-(2-Acetamidopyrimidin-4-yl) ethenylphenyl-3 oxamic acid tromethane salt | 2-acetamidopyrimidin-4-yl | H | H | 3-NHCOCOOH Tromethane salt | 195–197 |
| 18 | Ethyl 2-(3-pyridazinyl)ethenyl phenyl-4 oxamate | 3-pyridazinyl | H | H | 4-NHCOCOOC₂H₅ | 203–205 |

-continued

| Example No. | Nomenclature | A | $R_2$ | $R_3$ | NHCOCOOR$_1$ | m.p. °C. |
|---|---|---|---|---|---|---|
| 19 | 2-(3-Pyridazinyl)ethenylphenyl-4 oxamic acid ethanolamine salt | 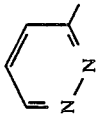 | H | H | 4-NHCOCOOH Ethanolamine salt | 199–201 |
| 20 | Ethyl 2-(2-pyrazinyl)ethenyl phenyl-4-oxamate | 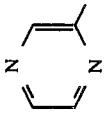 | H | H | 4-NHCOCOOC$_2$H$_5$ | 165–166 |
| 21 | 2-(2-Pyrazinyl)ethenylphenyl-4 oxamic acid sodium salt | 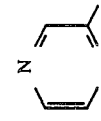 | H | H | 4-NHCOCOOH Sodium salt | >300 |
| 22 | Ethyl 2-(2-pyrazinyl)ethenyl phenyl-3 oxamate | 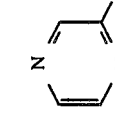 | H | H | 3-NHCOCOOC$_2$H$_5$ | 131–133 |
| 23 | 2-(2-Pyrazinyl)ethenylphenyl-3 oxamic acid ethanolamine salt | 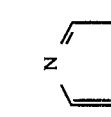 | H | H | 3-NHCOCOOH Ethanolamine salt | 205–208 |
| 24 | Ethyl 2-(2-methyl-6-ethoxyoxalyl-aminopyrimidin-4-yl)-ethenyl phenyl-4 oxamate | 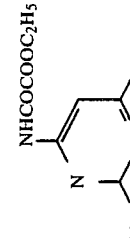 | H | H | 4-NHCOCOOC$_2$H$_5$ | 203–205 |
| 25 | 2-(2-Methyl-6-carboxycarbonyl-aminopyrimidin-4-yl)-ethenyl phenyl-4-oxamic acid hydrate diethanolamine salt | 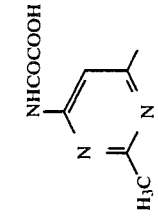 | H | H | 4-NHCOCOOH diethanolamine hydrate salt | 274–275 |

-continued

| Example No. | Nomenclature | A | R₂ | R₃ | NHCOCOOR₁ | m.p. °C. |
|---|---|---|---|---|---|---|
| 26 | Ethyl 2-(2-methyl-6-ethoxyoxalyl-aminopyrimidin-4-yl)-ethenyl phenyl-3 oxamate hemihydrate | 2-methyl-6-(NHCOCOOC₂H₅)-pyrimidin-4-yl ethenyl group | H | H | 3-NHCOCOOC₂H₅ hemihydrate | 197–199 |
| 27 | 2-(2-Methyl-6-carboxycarbonyl-aminopyrimidin-4-yl)-ethenyl phenyl-3-oxamic acid di-tromethane salt | 2-methyl-6-(NHCOCOOH)-pyrimidin-4-yl ethenyl group | H | H | 3-NHCOCOOH di-tromethane salt | 197–199 |
| 28 | Ethyl 2-(2-ethoxyoxalylamino pyrimidin-4-yl)-ethenylphenyl-3 oxamate | 2-(C₂H₅O−CO−CO−HN)-pyrimidin-4-yl ethenyl group | H | H | 3-NHCOCOOC₂H₅ | 199–201 |
| 29 | 2(2-Carboxycarbonylamino-pyrimidin-4-yl)ethenyl-phenyl-3 oxamic acid tetra-sodium salt dihydrate | 2-(⊖OOC−CO−N⊖)-pyrimidin-4-yl ethenyl group | H | H | 3-N⊖−COCOO⊖ tetra-sodium salt dihydrate | >350 |
| 30 | Ethyl 2-(3-ethylpyrazin-2-yl) ethenylphenyl-4 oxamate | 3-ethylpyrazin-2-yl | H | H | 4-NHCOCOOC₂H₅ | 143–145 |
| 31 | 2-(3-Ethylpyrazin-2-yl)ethenyl phenyl-4 oxamic acid ethanolamine salt | 3-ethylpyrazin-2-yl | H | H | 4-NHCOCOOH Ethanolamine salt | 173–175 |
| 32 | Ethoxyethyl 2-(2-pyrazinyl) ethenylphenyl-4 oxamate | 2-pyrazinyl | H | H | 4-NHCOCOOCH₂−CH₂OC₂H₅ | 122–124 |

-continued

| Example No. | Nomenclature | A | $R_2$ | $R_3$ | NHCOCOOR$_1$ | m.p. °C. |
|---|---|---|---|---|---|---|
| 33 | Ethoxyethyl 2-(2-methyl-6-amino-pyrimidin4-yl)-ethenylphenyl-4 oxamate hemihydrate | 4-amino-2-methyl-pyrimidinyl | H | H | 4-NHCOCOOCH$_2$—CH$_2$OC$_2$H$_5$ hemihydrate | 201–202 |
| 34 | Diethyl 2-(2-pyrazinyl)ethenyl phenyl-2,4-dioxamate | 2-pyrazinyl | H | 2-NHCOCO—OC$_2$H$_5$ | 4-NHCOCOOC$_2$H$_5$ | 172–174 |
| 35 | 2-(2-Pyrazinyl)ethenylphenyl-2,4 dioxamic acid diethanolamine salt | 2-pyrazinyl | H | 2-NHCOCOOH di-ethanol-amine salt | 4-NHCOCOOH | 193–196 |
| 36 | 2-(4-Pyrimidinyl)ethenyl phenyl-2,4 dioxamic acid diethanolamine salt | 4-pyrimidinyl | H | 2-NHCOCOOH di-ethanol-amine salt | 4-NHCOCOOH | n.d. |
| 37 | Diethyl 2-(6-chloro pyridazin-3-yl)ethenyl (4-chlorophenyl)-3,5 dioxamate | 6-chloro-pyridazinyl | 4-Cl | 3-NHCOCO—OC$_2$H$_5$ | 5-NHCOCOOC$_2$H$_5$ | 220–22 |

EXAMPLE 38

Passive Cutaneous Anaphylaxis (PCA) Assay

Representative compounds of the present invention were tested comparatively with cromoglycate to determine in vivo anti-allergic activity. The anti-allergic properties were ascertained in rats by the Passive Cutaneous Anaphylaxis test (PCA) essentially as described by Goose and Blair, Immunology, 16: 749–760 (1969).

Rat serum was diluted so that skin reactions with diameters between 10 and 15 mm in unsensitized rats were produced. The PCA test was performed in duplicate by injecting 0.1 ml of this antiserum dilution on each side of the shaved back of rats. Rats so treated were injected intravenously (i.v.) twenty-four hours later with 0.02 mg ovalbumin in 0.5 ml of 1% Evans Blue solution within five minutes after intravenous administration or 30 minutes after oral administration of the test compounds. Thirty minutes after the ovalbumin challenge the rats were killed by $CO_2$-asphyxiation, and the skin was reflected. The diameters, in millimeters, of the blued areas were measured and the mean diameter was determined. The circular area was calculated, and the mean area in square millimeters of the control group was considered as 100%. The results of the compound test groups were expressed as a percentage change from these control values. From dose response curves the dose reducing the size of the blued area by 50% ($ED_{50}$) was estimated.

The following table shows the results of this test:

| Compound of Example No. | Nomenclature | % Inhibition (10 mg/kg, p.o.) | $ED_{50}$ (mg/kg. p.o.) |
|---|---|---|---|
|  | Cromoglycate | n.d. | Inactive |
| 1 | Ethyl 2-(4-pyrimidinyl)ethenylphenyl-4 oxamate | n.d.* | 1.4 |
| 2 | 2-(4-Pyrimidinyl)ethenylphenyl-4 oxamic acid ethanolamine salt | 63% (3 mg/kg, i.v.) | n.d.* |
| 3 | Ethyl 2-(2-ethoxyoxalylaminopyrimidin-4-yl) ethenylphenyl-4 oxamate | n.d. | 10 |
| 4 | Ethyl 2-(4-pyrimidinyl)ethenylphenyl-3 oxamate | n.d. | 2.8 |
| 5 | 2-(4-Pyrimidinyl)ethenylphenyl-3 oxamic acid ethanolamine salt | n.d. | 12.3 |
| 6 | Ethyl 2-(4-pyrimidinyl)ethenylphenyl-2 oxamate | 20% | n.d. |
| 7 | 2-(4-Pyrimidinyl)ethenylphenyl-2 oxamic acid ethanolamine salt | n.d. | 8 |
| 8 | Ethyl 2-(4-pyrimidinyl)ethenyl-2-hydroxphenyl-4 oxamate | n.d. | 4.5 |
| 9 | Ethyl 2-(4-pyrimidinyl)ethenyl-5-chlorophenyl-3 oxamate | n.d. | 2 |
| 10 | Ethyl 2-(4-pyrimidinyl)ethenyl-3-N,N—dimethylaminoethoxyphenyl-4 oxamate | n.d. | n.d. |
| 11 | Ethyl 2-(4-pyrimidinyl)ethenyl-4-N,N—dimethylaminoethoxyphenyl-3 oxamate | 9% | n.d. |
| 12 | Diethyl 2-(4-pyrimidinyl)ethenylphenyl-2,4-dioxamate | n.d. | 2 |
| 13 | Ethyl 2-(2,6-diethoxypyrimidin-4-yl)ethenyl phenyl-4 oxamate | n.d. | 30 |
| 14 | Ethyl 2-(2-methyl-6-aminopyrimidin-4-yl)ethenyl phenyl-4 oxamate | n.d. | 10 |
| 15 | Ethyl 2-(6-methylpyrimidin-4-yl)ethenylphenyl-4 oxamate | n.d. | 1.1 |
| 16 | Ethyl 2-(2-acetamidopyrimidin-4-yl)ethenyl phenyl-3 oxamate | 42% | n.d. |
| 17 | 2-(2-Acetamidopyrimidin-4-yl)ethenylphenyl-3 oxamic acid tromethane salt | 37% | n.d. |
| 18 | Ethyl 2-(3-pyridazinyl)ethenylphenyl-4 oxamate | n.d. | 1 |
| 19 | 2-(3-Pyridazinyl)ethenylphenyl-4 oxamic acid ethanolamine salt | 0% | n.d. |
| 20 | Ethyl 2-(2-pyrazinyl)ethenylphenyl-4 oxamate | n.d. | 4.6 |
| 21 | 2-(2-Pyrazinyl)ethenylphenyl-4 oxamic acid sodium salt | n.d. | 10 |
| 22 | Ethyl 2-(2-pyrazinyl)ethenylphenyl-3 oxamate | n.d. | 4 |
| 23 | 2-(2-Pyrazinyl)ethenylphenyl-3 oxamic acid ethanolamine salt | n.d. | <1 |
| 24 | Ethyl 2-(2-methyl-6-ethoxyoxalylaminopyrimidin-4-yl)-ethenylphenyl-4 oxamate | n.d. | 0.3 |
| 25 | 2-(2-Methyl-6-carboxycarbonylaminopyrimidin-4-yl)-ethenylphenyl-4 oxamic acid hydrate diethanolamine salt | n.d. | 4.0 |
| 26 | Ethyl 2-(2-methyl-6-ethoxyoxalyl-aminopyrimidin-4-yl) ethenylphenyl-3 oxamate hemihydrate | 64% | <10.0 |
| 27 | 2-(2-Methyl-6-carboxycarbamyl-aminopyrimidin-4-yl)ethenyl-3 oxamic acid di-tromethane salt | 0% | 0.03 mg/kg, i.v. |
| 28 | Ethyl 2-(2-ethoxyoxalylamino-pyrimidin-4-yl) ethenyl-phenyl-3 oxamate | 5% | n.d. |
| 29 | 2-(2-Carboxycarbonylamino-pyrimidin-4-yl)ethenyl-phenyl-3 oxamic acid tetra-sodium salt di-hydrate | 67% (repeat 2%) | n.d. |
| 30 | Ethyl 2-(3-ethylpyrazin-2-yl)ethenylphenyl-4 oxamate | 6% | n.d. |
| 31 | 2-(3-Ethylpyrazin-2-yl)ethenyl-phenyl-4 oxamic acid ethanolamine salt | 15% | n.d. |
| 32 | Ethoxyethyl 2-(2-pyrazinyl)ethenylphenyl-4 oxamate | 46% | n.d. |
| 33 | Ethoxyethyl 2-(2-methyl-6-aminopyrimidin-4-yl)-ethenylphenyl-4 oxamate hemihydrate | 52% | n.d. |
| 34 | Diethyl 2-(2-pyrazinyl)ethenylphenyl-2,4-dioxamate | n.d. | n.d. |
| 35 | 2-(2-Pyrazinyl)ethenylphenyl-2,4 dioxamic acid di-ethanolamine salt | n.d. | 0.53 mg/kg, i.v. |
| 36 | 2-(4-Pyrimidinyl)ethenylphenyl-2,4 dioxamic acid di-ethanolamine salt | n.d. | 0.05 mg/kg, i.v. |
| 37 | Diethyl 2-(6-chloro pyridazin-3-yl)ethenyl(4-chlorophenyl)-3,5 dioxamate | 54% | n.d. |

*not determined

Pharmaceutical compositions containing the compounds according to the invention can be administered to warm-blooded animals orally, intravenously, perorally, parenterally, rectally or by the respiratory route. Such compositions generally include an inert pharmaceutical carrier and a therapeutically effective amount of the active ingredient.

When the compounds of formula I are given by the oral route, they can be formulated in the form of syrups, tablets, capsules (for example of gelatin), pills and the like. Preferably, the compositions are in unit dosage form, or in a form in which the patient can administer to himself a single dose. When the composition is in the form of a tablet, powder or lozenge, any pharmacuetical carrier suitable for formulating solid compositions may be used. Examples of such carriers are various starches, lactose, glucose, mannitol, sucrose, cellulose, methylcellulose, microcrystalline cellulose, talcum, pyrogenic silica, dicalcium phosphate, and high molecular weight polymers such as polyethylene glycol. Suitable liquid pharmaceutical carriers include glycerin, saline, water, propylene glycol or sorbitol solution, which may be compounded with flavoring or coloring agents to form syrups.

The compounds of this invention can also be prepared into compositions suitable for administration by other than the oral route. The compositions can be formulated, for example, for rectal administration as a suppository or for presentation in an injectable form in an aqueous or non-aqueous solution, suspension or emulsion in a pharmaceutically acceptable liquid, such as sterile, pyrogen-free water or a parenterally acceptable oil or a mixture of liquids, which may contain bacteriostatic agents, antioxidants, preservatives, buffers, or other solutes to render the solution isotonic with the blood, thickening agents, suspending agents or other pharmaceutically acceptable additives. Preservatives can include benzoic acid, methylene propylparaben, benzalkonium chloride or other quanternary ammonium compounds. Stabilizing agents, solubilizing agents and/or buffers conventionally used for injection solutions include, for example, tartrate, citrate and acetate buffers, ethanol, propylene glycol, polyethylene glycol, complex formers (such as EDTA), antioxidants (such as sodium bisulfate, sodium metabisulfate or ascorbic acid), high-molecular-weight polymers (such as liquid-polyethylene oxides) for viscosity regulation, and polyethylene derivatives of sorbitol anhydrides. Such forms can be presented in unit dose forms such as ampules or disposable injection devices or in multi-dose vials such as a bottle from which a appropriate dose may be withdrawn, or in solid form or concentrate which can be used to prepare an injectable formulation.

Compounds of this invention can also be suitably presented for administration to the respiratory tract as an aerosol or solution for a nebulizer, or as a microfine powder for insufflation, alone or in combination with an inert carrier such as lactose. In such a case the particles of active compounds suitably have diameters of less than 20 microns, preferably less than 10 microns. Where appropriate, small amounts of other anti-allergics, anti-asthmatics and bronchodilators, for example, sympathomimetic amines such as isoprenaline, isoetharine, metaproterenol, salbutamol, phenylephrine, fenoterol and ephedrine; xanthine derivatives such as theophylline and aminophylline; corticosteroids such as predenisolone and adrenal stimulants such as ACTH may be included.

Compounds of this invention may also be presented as an ointment, cream, lotion, gel, aerosol or solution for topical application to the nose or eye or as any of these and powders as topical applications to the skin.

In any of the foregoing formulations, a suitable dosage unit may contain from 1 to 500 mg of active ingredient. The effective dose of compounds of this invention depends on the particular compound employed, the condition of the patient and on the frequency and route of administration. In general it is orally administered in the range of from about 0.1 mg/kg to at least about 10 mg/kg body weight.

The following examples illustrate pharmaceutical dosage unit compositions comprising a compound of the present invention as an active ingredient and represent the best modes contemplated of using the invention. The parts are parts by weight unless otherwise specified.

EXAMPLE 39

| Tablets A tablet composition is compounded from the following ingredients: | |
| --- | --- |
| Ethyl 2-(2-methyl-6-ethoxyoxalylpyrimidin-4-yl)ethenylphenyl-4 oxamate | 0.010 parts |
| Stearic acid | 0.010 parts |
| Dextrose | 1.890 parts |
| TOTAL | 1.910 parts |

The ingredients are admixed in conventional manner, and the mixture is compressed into 1.91 g tablets, each of which is an oral dosage unit composition containing 10 mg of the active ingredient.

EXAMPLE 40

| Ointment An ointment composition is compounded from the following ingredients: | |
| --- | --- |
| Ethyl 2-(3-pyridazinyl)ethenylphenyl-4 oxamate | 2.000 parts |
| Fuming hydrochloric acid | 0.011 parts |
| Sodium pyrosulfite | 0.050 parts |
| Mixture (1:1) of cetyl alcohol and stearyl alcohol | 20.000 parts |
| White vaseline | 5.000 parts |
| Synthetic bergamot oil | 0.075 parts |
| Distilled water q.s. ad | 100.000 parts |

The ingredients are uniformly blended in conventional manner into an ointment, 100 g of which contain 2.0 g of the active ingredient.

EXAMPLE 41

| Inhalation aerosol An aerosol composition is compounded from the following ingredients: | |
| --- | --- |
| Ethyl 2-(4-pyrimidinyl)ethenylphenyl-4 oxamate | 1.00 parts |
| Soybean lecithin | 0.20 parts |
| Propellant gas mixture (Freon 11, 12 and 14) q.s. | 100.00 parts |

The ingredients are compounded in conventional manner, and the composition is filled into aerosol containers with a metering valve which releases 0.5 to 2.0 mg of active ingredient per actuation of the valve.

EXAMPLE 42

| Hypodermic solution A solution is compounded from the following ingredients: | |
| --- | --- |
| 2-(2-Methyl-6-carboxycarbonylamino-pyrimidin-4-yl)ethenylphenyl-4 oxamate diethanolamine salt | 5.0 parts |
| Sodium pyrosulfite | 1.0 parts |
| Sodium salt of EDTA | 0.5 parts |
| Sodium chloride | 8.5 parts |
| Double-distilled water q.s. ad | 1000.0 parts |

The individual ingredients are dissolved in a sufficient amount of double-distilled water, the solution is diluted to the indicated concentration with additional double-distilled water, the resulting solution is filtered until free from suspended particles, and the filtrate is filled under aseptic conditions into 1 ml-ampules which are subsequently sterilized and sealed. Each ampule contains 5 mg of the active ingredient.

Any one of the other compounds embraced by formula I or a nontoxic, pharmceutically acceptable salt thereof can be substituted for the particular active ingredient in the above formulation examples. Likewise, the amount of active ingredient in these illustrative examples can be varied to achieve the dosage unit range set forth above, and the amounts and nature of the inert pharmaceutical carrier ingredient can be varied to meet particular requirements.

While the present invention has been illustrated with the aid of certain specific embodiments thereof, it will be readily apparent to other skilled in the art that the invention is not limited to these particular embodiments and that various changes and modifications may be made without departing from the scope of the invention.

What is claimed is:

1. A compound of the formula

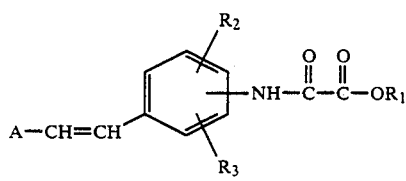

wherein
$R_1$ is hydrogen or alkyl of 1 to 4 carbon atoms;
$R_2$ is hydrogen, methyl, hydroxyl, alkoxy of 1 to 4 carbon atoms, di(alkyl of 1 to 2 carbon atoms) amino-(alkoxy of 1 to 4 carbon atoms) or halogen;
$R_3$ is hydrogen or $NHCOCOOR_1$;
A is

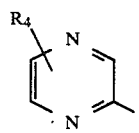

$R_4$ is hydrogen, methyl, alkoxy of 1 to 4 carbons atoms, hydroxyl, amino, alkanoyloxy of 1 to 2 carbon atoms, di(alkyl of 1 to 2 carbon atoms)-amino-(alkoxy of 1 to 4 carbon atoms) or acetamido; and
$R_5$ is hydrogen, amino, alkoxy of 1 to 4 carbon atoms, halogen or $NHCOCOOR_1$;
or, when $R_1$ is hydrogen, a nontoxic, pharmaceutically acceptable salt thereof.

2. A compound of claim 1 wherein $R_4$ is hydrogen or methyl.

3. The compound of claim 2 which is ethyl 2-(2-pyrazinyl)ethenylphenyl-4 oxamate.

4. The compound of claim 2 which is 2-(2-pyrazinyl)ethenylphenyl-4 oxamic acid sodium salt.

5. The compound of claim 2 which is ethyl 2-(2-pyrazinyl)ethenylphenyl-3 oxamate.

6. The compound of claim 2 which is the ethanolamine salt of 2-(2-pyrazinyl)ethenylphenyl-3 oxamic acid.

7. The compound of claim 2 which is ethyl 2-(3-ethyl-pyrazin-2-yl)ethenylphenyl-4 oxamate.

8. The compound of claim 2 which is 2-(3-ethylpyrazin-2-yl)ethenylphenyl-4 oxamic acid ethanolamine salt.

9. The compound of claim 2 which is ethoxyethyl 2-(2-pyrazinyl)ethenylphenyl-4 oxamate.

10. The compound of claim 2 which is diethyl 2-(2-pyrazinyl)ethenylphenyl-2,4 dioxamate.

11. The compound of claim 2 which is 2-(2-pyrazinyl)ethenylphenyl-2 4 dioxamic acid diethanolamine salt.

12. A composition comprising an effective antiallergic amount of a compound of claims 1 or 2 and a nontoxic, pharmaceutically acceptable carrier.

13. A composition comprising an effective antiinflammatory amount of a compound of claims 1 or 2 and a nontoxic, pharmaceutically acceptable carrier.

14. A method of treating an allergic disorder in a mammal in need thereof, which comprises administering an effective amount of a compound of claims 1 or 2 to said mammal.

15. A method of treating an inflammatory disorder in a mammal in need thereof, which comprises administering an effective amount of a compound of claims 1 or 2 to said mammal.

* * * * *